United States Patent
Clement et al.

(10) Patent No.: US 10,463,814 B2
(45) Date of Patent: Nov. 5, 2019

(54) INSUFFLATION NEEDLE

(71) Applicant: KVI LLC, Eden Prairie, MN (US)

(72) Inventors: Thomas P. Clement, Bloomington, IN (US); S. Stone Linton, Bloomington, IN (US)

(73) Assignee: KVI LLC, Eden Prairie, MN (US)

( * ) Notice: Subject to any disclaimer, the term of this patent is extended or adjusted under 35 U.S.C. 154(b) by 497 days.

(21) Appl. No.: 15/260,782

(22) Filed: Sep. 9, 2016

(65) Prior Publication Data
US 2017/0087310 A1  Mar. 30, 2017

Related U.S. Application Data (60) Provisional application No. 62/216,784, filed on Sep. 10, 2015.

(51) Int. Cl.
| | | |
|---|---|---|
| *A61M 13/00* | (2006.01) | |
| *A61B 17/34* | (2006.01) | |
| *A61M 39/22* | (2006.01) | |
| *A61B 90/00* | (2016.01) | |

(52) U.S. Cl.
CPC ....... *A61M 13/003* (2013.01); *A61B 17/3423* (2013.01); *A61B 17/3474* (2013.01); *A61B 17/3496* (2013.01); *A61B 17/3498* (2013.01); *A61B 90/08* (2016.02); *A61M 39/22* (2013.01); *A61B 2017/3456* (2013.01); *A61B 2090/0811* (2016.02); *A61M 2039/229* (2013.01); *A61M 2205/584* (2013.01); *A61M 2205/586* (2013.01)

(58) Field of Classification Search
CPC ................ A61M 13/003; A61M 39/22; A61M 2039/229; A61M 2205/584; A61B 17/3423; A61B 17/3474; A61B 17/3496; A61B 17/3498; A61B 2017/3456
See application file for complete search history.

(56) References Cited

U.S. PATENT DOCUMENTS

| | | | | |
|---|---|---|---|---|
| 6,447,483 B1* | 9/2002 | Steube | ............... | A61B 17/3415 604/158 |
| 2012/0209167 A1* | 8/2012 | Weber | ................ | A61M 13/003 604/26 |

* cited by examiner

*Primary Examiner* — Laura A Bouchelle
*Assistant Examiner* — Dung T Ulsh
(74) *Attorney, Agent, or Firm* — Schwegman Lundberg & Woessner, P.A.

(57) ABSTRACT

A medical apparatus which comprises a sharpened outer cannula and a blunt inner cannula slidingly disposed within the outer cannula is configured to allow one-hand operation by user to operate the medical apparatus. The apparatus also contains a visual position indication system adapted to indicate the position of the inner cannula.

17 Claims, 6 Drawing Sheets

INSUFFLATION NEEDLE

This application claims priority under 35 U.S.C. § 119 to U.S. Provisional Application Ser. No. 62/216,784 entitled "INSUFFLATION NEEDLE," which was filed on Sep. 10, 2015, the entirety of which is incorporated herein by reference.

BACKGROUND

The present disclosure relates to medical instruments. More particularly, the present disclosure relates to an apparatus and method for safely puncturing body tissue. More specifically, the disclosure relates to a surgical instrument having at least a single position indication system to positively indicate both when the puncturing portion is in a protective position and when it is in a non-protective position.

In various medical procedures, one or more surgical instruments may be used to puncture or penetrate body tissue. The body tissue may be penetrated in order to insert the instrument into a body cavity such as, for example, the abdominal cavity. Throughout the present application, the terms penetrating, piercing and puncturing and formatives thereof are used interchangeably. For example, an instrument known as a trocar that generally comprises a sharp pointed instrument, may be used to penetrate the abdominal wall to create an access hole therethrough into the abdominal cavity. In another example, an instrument known as a Veress needle or insufflation needle may be used. Veress-type needles use a hollow, blunt inner needle capable of fluid passage, and to carry insufflating gas into the abdominal cavity.

Needles to create pneumoperitoneum are used to insufflate the abdominal cavity to facilitate endoscopic examination and surgery. Laparoscopic surgical procedures require that a fluid or gas, such as carbon dioxide, be introduced into the abdominal cavity. This establishes pneumoperitoneum wherein the peritoneal cavity is sufficiently inflated for the insertion of trocars into the abdomen. The fluid may be introduced using a Veress or insufflation needle.

A Veress-type pneumoneedle has a spring-loaded, blunt tipped inner needle contained within a larger diameter piercing needle. The larger diameter needle is hollow and allows for passage of the blunt needle therein. In using such a needle, a user or user illustratively pushes the free end of the cannula against the body tissue, muscles and/or membranes forming the cavity wall of, for example, the abdomen of a patient.

Once the Veress-type needle penetrates the abdominal wall and enters the body cavity, the resistance against the end of the Veress-type needle is removed, so that the spring force causes the blunt needle or cannula to move forward, to extend beyond the sharp tip of the outer needle. This allows the needle to enter the body without puncture or laceration of any abdominal structures. In other words, the cannula retracts against the spring biasing, permitting the relatively sharper needle end to be forced, for example, through the abdominal wall into the abdominal cavity, whereafter the free end of the relatively blunt inner cannula pops out or extends from the relatively sharp needle via the spring biasing, thereby exposing the gas exit hole or aperture. This assumes that the needle is in an open area of the illustrative abdominal cavity or other body cavity and is not pushing against some other body tissue such as, for example, an internal organ or muscle, which would prevent the inner cannula from so popping out or moving to its extended position relative to the needle.

The physician can then connect a gas line to the valve or petcock and cause gas to enter into the Veress needle, pass through the cannula and exit out of the gas exit hole of the cannula into the abdominal cavity for insufflating the abdominal cavity. Alternatively, fluid can either be forced into or sucked from the abdominal cavity or other body cavity through use of the Veress needle.

If the needle goes beyond the peritoneum, the needle may perforate the stomach, small bowel, colon, bladder, or major vascular structures, the consequences of which can be fatal. The purpose of the spring-loaded safety tip of the Veress needle is to minimize the risk of visceral injury by covering the sharp tip once it has penetrated the peritoneum and reached a void. Generally, the surgeon relies on tactile senses to determine the proper placement of the needle by recognizing when the needle is inserted through the fascia and then through the peritoneum. However, this technique is often unreliable. It is sometimes difficult for a user, physician or surgeon to ascertain when the internal cavity wall has been breached by the Veress needle or trocar. Typically, the only indication is a reduction in the amount of resistance felt by the surgeon, with perhaps a mechanical vibration or sound caused by the forward movement of the spring biased needle or stylet once the internal cavity has been breached. Various devices have been developed to provide a more positive indication of when the cavity wall has been breached. These devices typically utilize visual or audible signals.

Some relevant examples of Veress needle and trocar instruments include Bauer et al., U.S. Pat. No. 4,379,458; Yoon, U.S. Pat. No. 4,535,773; Moll, U.S. Pat. No. 4,601,710; Moll et al., U.S. Pat. No. 4,654,030; Warring, U.S. Pat. No. 4,808,168; Adair, U.S. Pat. No. 4,869,717; Lander, U.S. Pat. No. 4,902,280; and Holmes, U.S. Pat. No. 4,931,042; Kulkashi et al., U.S. Pat. No. 5,098,388; Sewell, Jr., U.S. Pat. No. 5,290,276; Smith et al., U.S. Pat. No. 5,256,148; Scarfone et al., U.S. Pat. No. 5,669,883; Dennis, U.S. Pat. No. 5,853,392; Buncke et al., U.S. Pat. No. 6,245,091; and Clementine et al., U.S. Pat. No. 8,840,588; the disclosures of all of which are now expressly incorporated herein by reference.

After establishing pneumoperitoneum, the next step in laparoscopic surgery involves the insertion of a trocar into the abdominal cavity. It is through this first trocar that an endoscope is inserted into the abdominal cavity to provide the surgeon with a view of the rest of the operation. Trocars are similar to the Veress needle in that they are also equipped with a spring-loaded safety shield to avoid visceral injury. Trocars, like Veress needles, are inserted using a sudden thrust of the pointed tip into the abdomen. Therefore, as is true with the Veress needle, placement of the trocar is also vital, and the reliance of the surgeon on mere tactile senses for proper placement can be fatal.

SUMMARY OF THE INVENTION

The present invention may comprise one or more of the features and combinations thereof set out below or in the claims appended hereto.

According to one aspect of the present disclosure, a medical apparatus comprises a handle, a gas actuating switch, an outer cannula, an inner cannula, a position indication system, a gas actuating switch, and a bias member. The handle has an interior chamber defined between a distal end and an operative end of the handle. The gas actuating switch includes a sliding member and a lever. The sliding member is positioned at a superior surface of the handle. The outer cannula includes a proximal end and a distal end. The proximal end is coupled to the operative end of the handle and the distal end includes a sharpened tip. The inner cannula also includes a proximal end and a distal end. The distal end includes a blunt tip. The inner cannula is slidably disposed within the outer cannula. The position indication system includes a first indicating member and a second indicating member disposed within the interior chamber of the handle. The first and second indicating members are visible through at least one viewing window. Moreover, the first indicating member includes at least one shaped puncture visible through the viewing window to indicate a position of the inner cannula. The bias member includes a front end and a rear end. The bias member is disposed within the interior chamber between the position indication system and the proximal end of the inner cannula. When a force sufficient to overcome the normal force of the bias member is applied to the blunt tip of the inner cannula, the inner cannula moves to a retracted position wherein the blunt tip no longer extends beyond the sharpened tip of the outer cannula.

In some embodiments, the viewing window extends 360 degrees around the position indication system about a longitudinal axis of the medical apparatus.

In some embodiments, each viewing window is configured to align with each shaped puncture.

In some embodiments, the first indicating member is slidably coupled to the second indicating member to indicate a position of the inner cannula relative to the outer cannula. The second indicating member is stationary and is affixed at the operative end of the handle.

In some embodiments, the first indicating member comprises a positive indicating member and the second indicating member comprises a negative indicating member. The positive indicating member is perceptible when the inner cannula is in the extended position, and the negative indicating member is perceptible when the inner cannula is in the retracted position.

In some embodiments, the positive indicating member is a first color and the negative indicating member is a second color that is different than the first color.

In some embodiments, the positive indicating member comprises the shaped puncture which extends through the positive indicating member thereby exposing a part of the second color of the negative indicating member positioned beneath the shaped puncture.

In some embodiments, the gas actuating switch is configured to control gas flow of the medical apparatus by engaging a resilient tube operatively connecting the distal end and the operative end of the handle to conduct gas, the sliding member of the gas actuating switch is slidably movable between a first position and a second position along the handle.

In some embodiments, the gas activation system is positioned on the superior surface of the handle to allow a one-hand operation.

In some embodiments, the handle is ergonomically designed such that the distal end of the handle is tapered and angled toward the floor so that the medical device is held by the user's fingers pressing the medical device against a heel of the hand, leaving the thumb free for movement to control the gas actuating switch.

According to another aspect of the present disclosure, a medical apparatus comprises a stopcock switch, an outer cannula, an inner cannula, and a position indication system. The stopcock switch is configured to control gas flow of the medical apparatus. The outer cannula has a first end and a second end, the first end coupled to the operative end of the handle, and the second end comprising a sharpened tip. The inner cannula is slidably coupled to the outer cannula. The inner cannula has a first end and a second end, the first end coupled to a bias member, the second end comprising a blunt tip that extends outwardly beyond the sharpened tip of the outer cannula. The position indication system has a first indicating member, a second indicating member, and the bias member. The first and second indicating members are visible through a clear viewing window to indicate a position of the inner cannula. The viewing window further extending 360 degrees circumferentially around the position indication system. The position indication system is configured to be coupled to the outer and inner cannulas at a first end and the stopcock switch at a second end opposite the first end. When a force sufficient to overcome the normal force of the bias member is applied to the blunt tip at the second end of the inner cannula, the first end of the inner cannula forces the bias member to retract such that the blunt tip no longer extends beyond the sharpened tip of the outer cannula.

In some embodiments, wherein the first indicating member is slidably coupled to the second indicating member to indicate a position of the blunt tip of the inner cannula relative to the sharpend tip of the outer cannula. The second indicating member is stationary and is affixed to the position indication system.

In some embodiments, the first indicating member comprises a positive indicating member and the second indicating member comprises a negative indicating member. The positive indicating member is perceptible when the blunt tip exposed beyond the sharpened tip, and the negative indicating member is perceptible when the sharpened tip is exposed beyond the blunt tip.

In some embodiments, the positive indicating member is a first color and the negative indicating member is a second color that is different than the first color.

In some embodiments, the positive indicating member includes a plurality of teeth arranged around a circumference of the second indicating member.

In some embodiments, wherein each tooth has an arrow shape with an arrowhead pointing to the sharpened tip of the outer cannula.

In some embodiments, the medical apparatus further comprises an ergonomically designed handle coupled to the stopcock switch opposite the position indication system.

Further provided is a method of performing a medical procedure comprising the steps of: providing a puncturing apparatus comprising nested hollow tubes in sliding relationship to one another, the nested hollow tubes comprising an outer cannula and an inner cannula, urging the inner cannula to an extended position wherein a distal end of the inner cannula extends beyond a distal end of the outer cannula, applying a force against the distal end of the inner cannula to urge the inner cannula to a retracted position wherein the distal end of the inner cannula does not extend beyond the distal end of the outer cannula, and providing a visual position indication system having a first indicating member and a second indicating member, wherein the visual position indication system provides the first indication when the inner cannula extends beyond the outer cannula and a second indication when the inner cannula does not extend beyond the distal end of the outer cannula.

In some embodiments, the first indicating member is slidably coupled to the second indicating member to indicate a position of the inner cannula relative to the outer cannula.

In some embodiments, the method further comprises a step of actuating a gas actuating switch by (i) forcing the gas actuating switch forwardly away from the heel of the user's hand using the thumb or other digit of the user by pressing the cradle portion against the heel of the user's hand to introduce a gas flow through the inner cannula to the body cavity, and (ii) forcing the gas actuating switch backwardly toward the heel of the user's hand using the thumb or other digit of the user to halt the gas flow.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
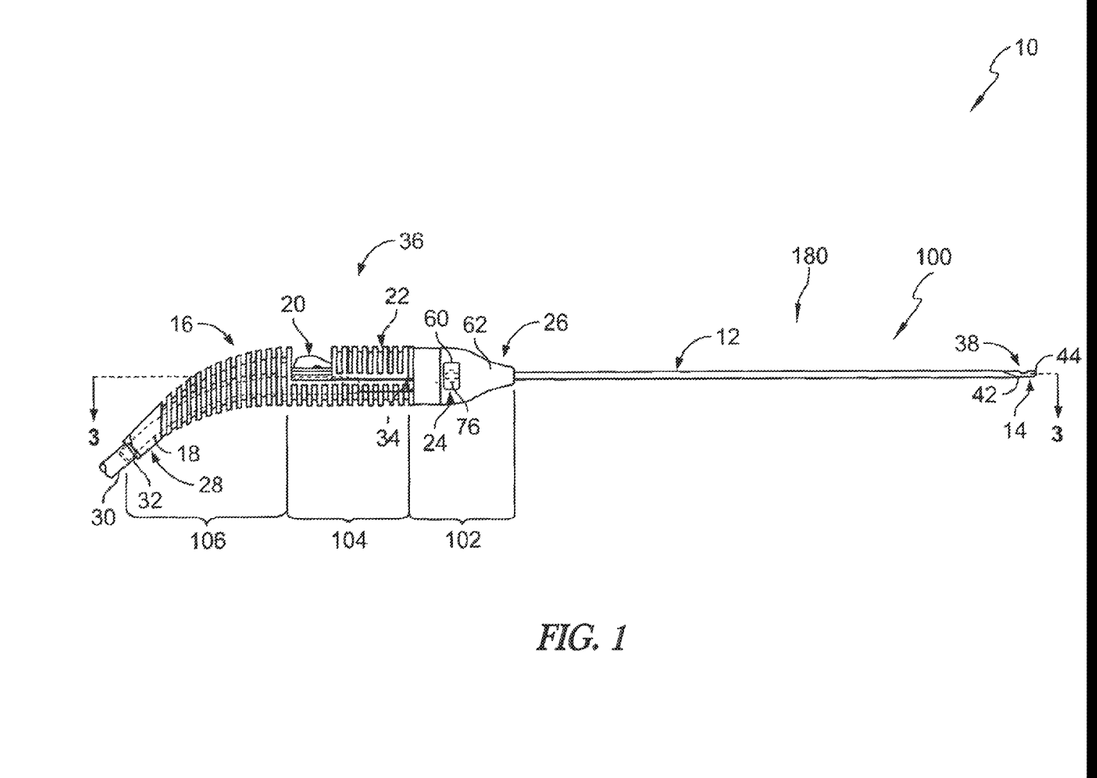
FIG. 1 is a side view of a surgical apparatus.
Figure 2:
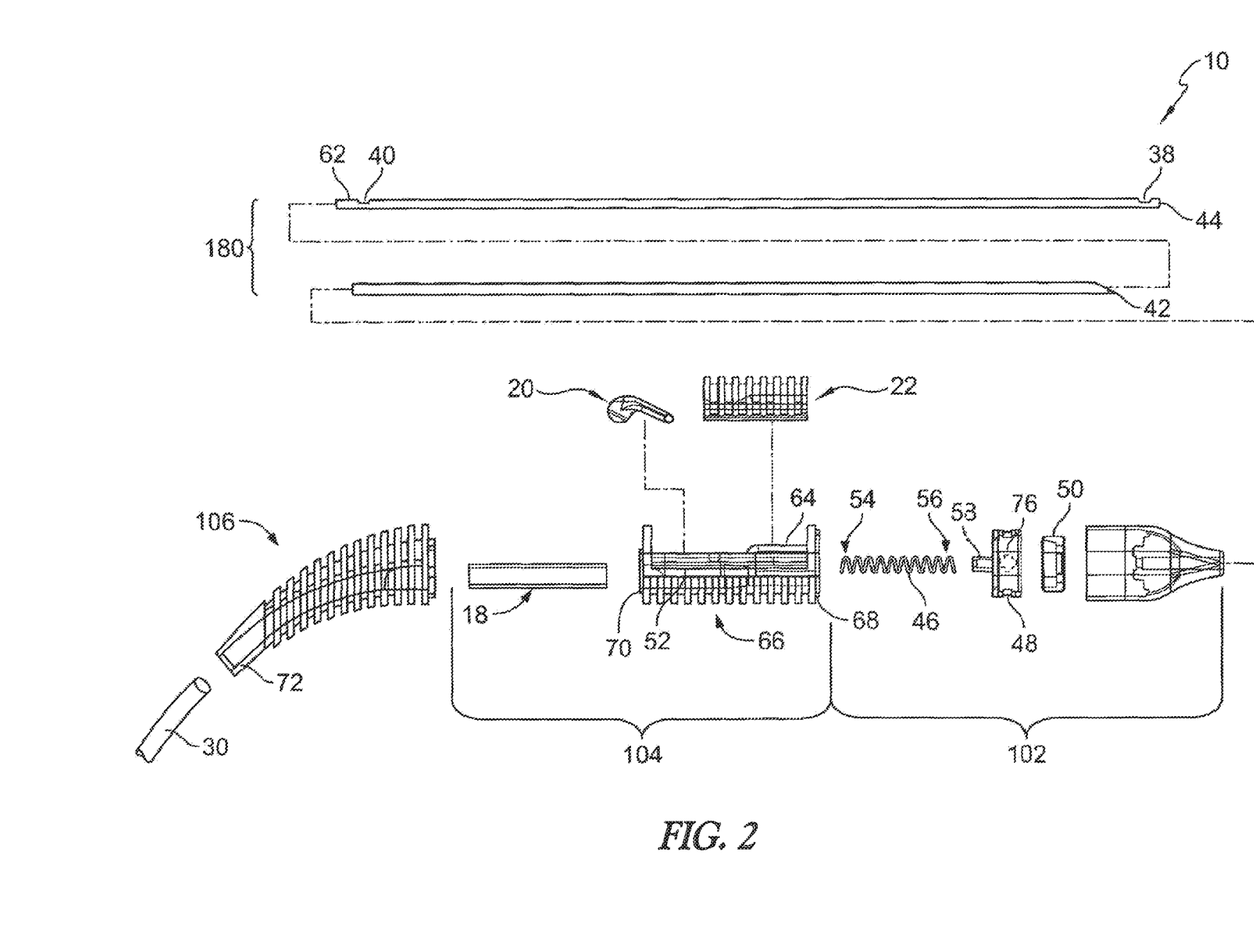
FIG. 2 is an exploded view of the surgical apparatus of FIG. 1.
Figure 3:
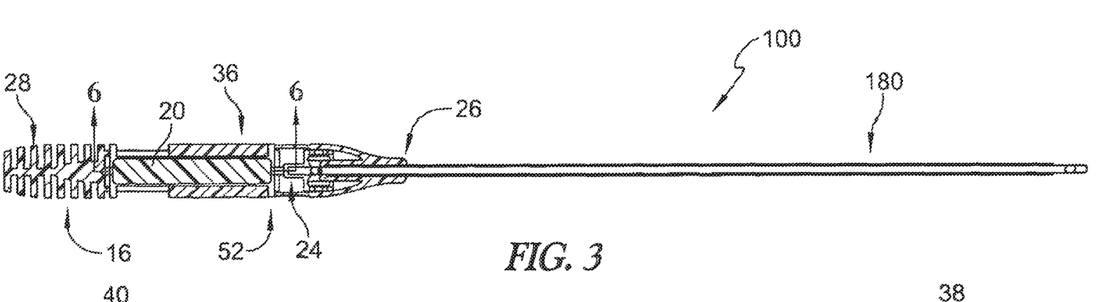
FIG. 3 is a cross section view taken along the line 3-3 in FIG. 1 showing the insufflation needle.
Figures 4, 4A, 4B:
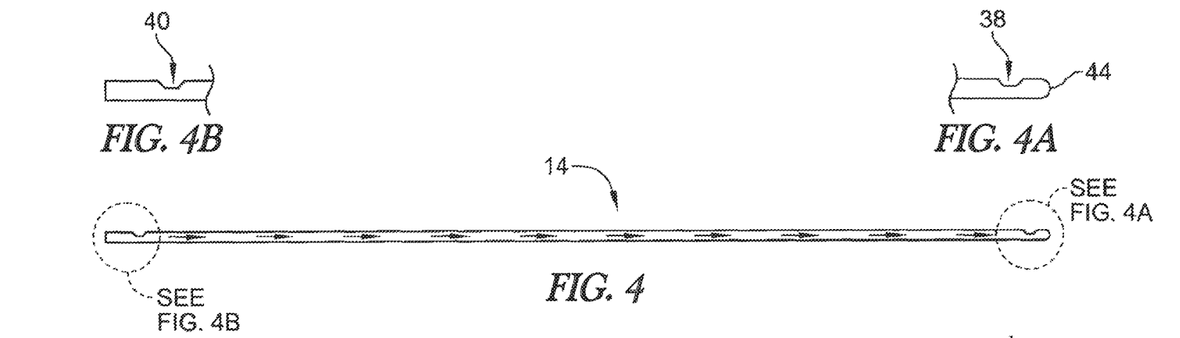
FIG. 4 is a side view of an inner cannula of the insufflation needle of FIG. 1 showing two sufflation holes.
Figures 5, 5A:
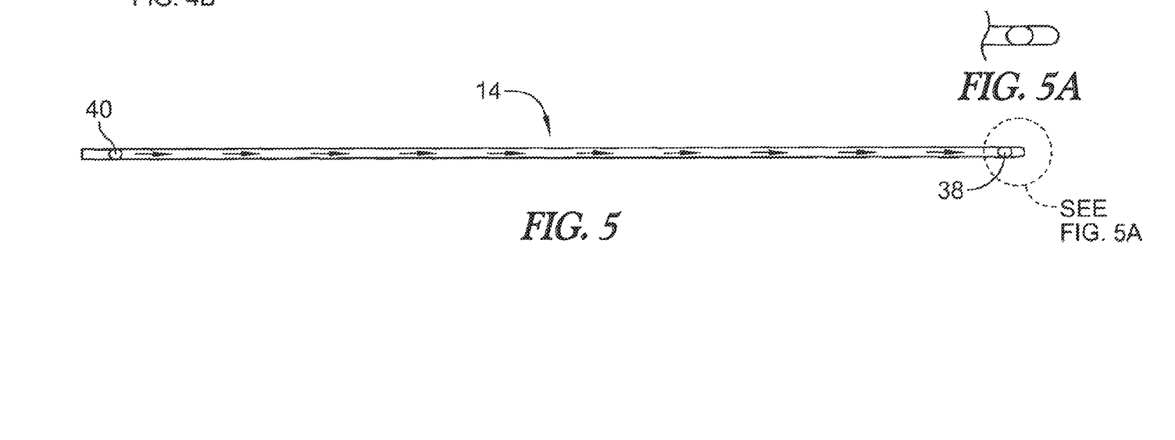
FIG. 5 is a top plan view of the inner cannula of the insufflation needle of FIG. 1 showing two sufflation holes.
Figure 6:
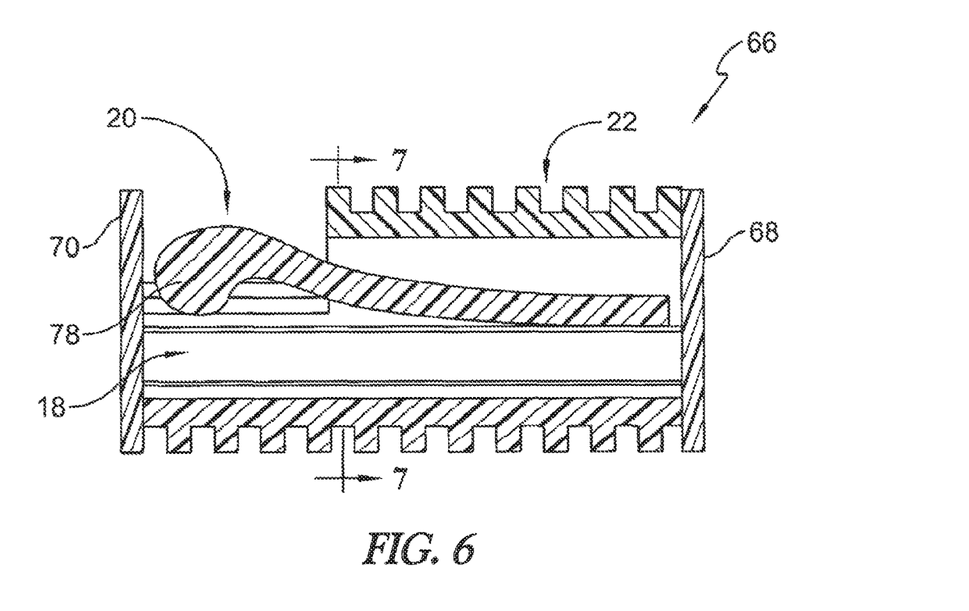
FIG. 6 is a cross section view taken along the line 6-6 in FIG. 3 showing a switch section of a handle showing a gas activation switch in its released position which allows fluid or gas to flow into the insufflation needle.

An illustrative embodiment of a medical apparatus 10 is shown in FIG. 1. The medical apparatus 10 is used to puncture an anatomical organ structure such as for example and without limitation a cavity wall and providing a passageway via the puncture wound for communicating with the interior of the cavity. The medical apparatus 10 comprises a handle 16, a gas actuating switch 36, a position indication system 24, and an insufflation needle 80. The handle 16 is designed to provide an ergonomic grip and comprises of three sections: a head section 82, a switch section 84, and a tail section 86, as shown in FIG. 2. The handle 16 is proportioned and shaped to be held generally by the index and middle fingers pressing the switch section 84 and the tail section 86 against a heel of the hand of a user of the medical device 10, leaving the thumb free for movement to control the medical device 10. Accordingly, the tail section 86 of the handle 16 is illustratively curved downwardly away from the switch section 84 and the head section 82 in order to provide leverage to the user when using the medical apparatus 10. In addition, one-hand operation is achieved by the gas actuating switch 36 positioned on a superior surface of the handle 16 which allows the user to use the thumb to engage the gas actuating switch 36.

The handle 16 has a rear distal end 28 and a front operative end 26. The operative end 26 of the handle 16 is coupled to the insufflation needle 80 and the distal end 28 of the handle 16 is coupled to a supply tube 30 that is configured to supply fluid or gas to the insufflation needle 80. The insufflation needle 80 is made up of a hollow outer cannula 12 and an inner cannula 14. As shown in FIGS. 1 and 2, the outer cannula 12 and the inner cannula 14 are generally elongated. The inner cannula 14 has a smaller diameter than the hollow outer cannula 12 so that the inner cannula 14 is slidably received within and extends through the outer hollow cannula 12. The outer cannula 12 and the inner cannula 14 each have a distal end and a proximal end. The proximal ends of both the outer cannula 12 and the inner cannula 14 are coupled to the operative end 26 of the handle 16. The distal end of the outer cannula 12 has a sharpened tip 42 that is relatively sharp to provide a means for puncturing body tissue, whereas the distal end of the inner cannula 14 has a blunt tip 44 relative to the sharpened tip 42. The inner cannula 14 further includes two side sufflation holes or apertures, a sufflation outlet aperture 38 and a sufflation inlet aperture 40, to conduct the fluid or gas to the distal end of the insufflation needle 80, as will be described in more detail below.

The handle 16 further includes a hollow interior cavity or bore 52 extending for a portion of the length of handle 16 containing narrow walls, in a generally cylindrical fashion. The proximal end of the outer cannula 12 is coupled to the operative end 26 of the handle 16. The proximal end of the inner cannula 14, on the other hand, extends through the operative end 26 and into the head section 82 of the handle 16 where it is received by the position indication system 24. The head section 82 of the handle 16 further enhouses the bias member 46 coupled to the position indication system 24. The bias member 46 is positioned at a rear end 54 of the head section 82 between a front end of the switch section 84 and the position indication system 24 in the head section 82. When the force is applied to the distal blunt tip 44 of the inner cannula 14, the proximal end of the inner cannula 14 is pushed against the position indication system 24 and thus transferring the force to the bias member 46, for example a spring, that is attached to the position indication system 24. The bias member 46 allows the inner cannula 14 to move between an extended position and a retracted position relative to the outer cannula 12. The extended position is a protective and safe position which allows the blunt tip 44 of the inner cannula 14 to extend past or beyond the sharpened tip 42 of the outer cannula 12. The retracted position is an exposed and unsafe position in which the bias member 46 is compressed and in which sharpened tip 42 of the outer cannula 12 is exposed in order to puncture body tissue.

When assembled, the blunt tip 44 of inner cannula 14 is caused by the normal force of the extended bias member 46 to extend past the sharpened tip 42 of the hollow outer cannula 12. In operation, when the user proceeds to insert the insufflation needle 80 into a patient's body by applying pressure against the handle 16, the opposite pressure, or resistance of the cavity wall of the patient is exerted against the distal end of the insufflation needle 80. The resistance is first exerted against the blunt tip 44 of the inner cannula 14 when it contacts body tissue thereby causing insufflation needle 80 to retract against the normal extending bias force of the bias member 46 and into the handle 16 of the medical apparatus 10.

Upon retraction, the blunt tip 44 of the inner cannula 14 will no longer extend beyond the sharpened tip 42, and the body tissue or wall of the patient will instead contact the sharpened tip 42 of the outer cannula 12. As the user continues to apply inserting pressure, the sharpened tip 42 will eventually pierce the body tissue or body wall. Subsequent to piercing the body tissue or body wall, the bias force of the bias member 46 is again greater than the generally opposing tissue force and the bias member 46 again biases, pushes or extends the inner cannula 14 outwardly from the handle 16 until the blunt tip 44 of the inner cannula 14 is caused to extend beyond or past the sharpened tip 42 of the outer cannula 12. Thus, without compressional forces applied at distal blunt tip 44 of inner cannula 14, the bias member 46 normally biases inner cannula 14 toward the extended position generally outwardly away from the handle 16. Those skilled in the art will understand that this operation allows the blunt tip 44 of the inner cannula 14 to protect body tissue, for example and without limitation the internal abdominal cavity, from damage by the sharpened tip 42 of the outer cannula 12.

The position of the blunt tip 44 of the inner cannula 14 is relative to the sharpened tip 42 of the outer cannula 12. As described above, the inner cannula 14 is in the extended position if the blunt tip 44 of inner cannula 14 is extended outwardly beyond the sharpened tip 42 of the outer cannula 12. Whereas, the inner cannula 14 is in the retracted position if the blunt tip 44 of inner cannula 14 is retracted inwardly exposing the sharpened tip 42 of the outer cannula 12. The position of the inner cannula 14 is illustratively indicated by the position indication system 24.

In the illustrative embodiment, the position indication system 24 of the medical apparatus 10 is a visible indication system which comprises two position indicating members: a first indicating member 48 and a second indicating member 50. However, it will be appreciated that in some embodiment, the medical apparatus 10 may comprise a plurality of the position indication systems with different perceptible means. For example and without limitation, the position indication system may comprise the visible indication system, an audible or aural indication system, or a tactile indication system. The medical apparatus 10 may comprise, for example, a combination of a visible indication system and a tactile indication system, may comprise a combination of a visible indication system and an audible indication system, and may comprise a combination of a visible indication system, a tactile indication system, and an audible indication system. Further, the visual indication system may comprise a mechanical indication system, an electronic indication system, a chemical indication system, an infra-red indication system, a visible light indication system, a radio frequency indication system or any combination of the foregoing, for example and without limitation an electromechanical indication system. Of course, there may be more than one type of visual indication system, alone or in combination with one or more of the other types of indication systems.

The position indication system 24 is disposed in the bore 52 of the handle 16 and is positioned near the operative end 26 of the handle 16. As shown in FIG. 1, the handle 16 illustratively is made of opaque plastic. The position indication system 24 is visible through clear or transparent viewing windows 60 located on each of the lateral sides of the operative end 26 of the handle 16. In addition, in some embodiment, the viewing window 60 may comprise a magnifying lens or window to allow the user to better view the first or second indicating member. In some embodiments, the viewing window 60 may extend less than 360 degrees, for example, 180 degrees around the position indication system 24 about a longitudinal axis 88 of the medical apparatus 10. Such viewing window may be positioned on a right surface, a left surface, or an upper surface of the position indication system 24. In some embodiments, the viewing window 60 may extend 360 degrees around the position indication system 24 of the handle 16 about the longitudinal axis 88 of the medical apparatus 10, such that the position indicating members 48, 50 are visible from any angle of view.

The second indicating member 50 is stationary and is affixed near the operative end 26 of the handle 16. The first indicating member 48 is slidably coupled to the second indicating member 50. The first indicating member 48 has a protrusion 58 extending distally from a rear surface of the first indicating member 48, as shown in FIG. 2. The first indicating member 48 has a bulged surface facing the distal end 28 of the handle 16 and a cavity surface facing the operative end 26 of the handle 16. The bulged side of the first indicating member 48 is coupled to a front end 56 of the bias member 46 so that the protrusion 58 is received by the bias member 46. The cavity surface of the first indicating member 48 is configured to receive the proximal tip 62 of the inner cannula 14. Specifically, the proximal tip 62 of the inner cannula 14 extends through the second indicating member 50 and is received by the cavity of the first indicating member 48.

The position indication system 24 is configured to indicate whether the inner cannula 14 is in the extended position or the retracted position relative to the outer cannula 12. The inner cannula 14 is in the extended position when no force is applied to the distal blunt tip 44 of the inner cannula 14 and the blunt tip 44 of inner cannula 14 is extended outwardly beyond the sharpened tip 42 of the outer cannula 12. When the inner cannula 14 is in the extended position, the front end 56 of bias member 46 is placed against the bulged side of the protrusion 58 and exerts a normally extending force against the first indicating member 48. When the inner cannula 14 is being forced outwardly away from the handle 16, the first indicating member 48 is positioned on top of the second indicating member 50, such that an inferior surface of the first indicating member 48 is in contact with a superior surface of the second indicating member 50. Therefore, during the extended position, only the first indicating member 48 is exposed to or aligned with the viewing window 60.

As the force is being exerted on the blunt tip 44 of the inner cannula 14, the force is transferred against the first indicating member 48 and compresses the bias member 46. When the bias member 46 is compressed, the inner cannula 14 is in its retracted position, such that the blunt tip 44 of inner cannula 14 is retracted inwardly exposing the sharpened tip 42 of the outer cannula 12. As the inner cannula 14 is being forced inwardly toward the handle 16, the proximal tip 62 of the inner cannula 14 forces the first indicating member 48 toward the handle 16. Therefore, during the retracted position, the first indicating member 48 is no longer on top of the second indicating member 50, and only the second indicating member 50 is exposed to or aligned with the viewing window 60 while first indicating member 48 is obscured by opaque portions of the handle 16.

The position indication system 24 illustratively includes a dual color array having the first indicating member and the second indicating member in different colors. As described above, the first indicating member 48 slides over the second indicating member 50. The first indicating member 48 is colored in a positive manner, such as for example and without limitation green. The second indicating member 50 is colored in a negative fashion, such as for example and without limitation red. Illustratively, the desired colors could be chosen from any desired color in the color spectrum as further described herein. Illustratively, the colors are different and contrast. In this way, when the inner cannula 14 is in its protective extended position, it is fully extended past the sharpened tip 42 of the outer cannula 12. Only the first, illustratively green, or positive indicating member 48 is exposed to or aligned with the viewing window 60 so that it can be perceived, sensed or seen by the user. The second negative indicating member 50 is obscured and not perceptible or sensible when the blunt tip 44 of the inner cannula 14 extends past or beyond the sharpened tip 42. However, when the blunt tip 44 is retracted, for example by resistance or a force applied to the blunt tip 44 of inner cannula 14 by for example body tissue, the second indicating member 50, illustratively red, is exposed to or aligned with the viewing window 60 so that the user perceives, senses or sees the negative indicating member in the viewing window 60. In this fashion, the viewer knows that the sharpened tip 42 of the outer cannula 12 is exposed, and that there is a likelihood of harm to the patient if the inner cannula 14 does not return to its initial extended position.

In some embodiments, the first indicating member may have a shaped puncture 76 to further distinguish between the first indicating member and the second indicating member so that position indicating members are easily perceived by the user. The shaped puncture 76 is helpful especially for color-blind users using the medical apparatus 10. Illustratively, the desired shapes could be chosen from any shape. For example and without limitation any shape of circle, semicircle, oval, crescent, star, heart, hourglass, and any polygon, including but not limited to, triangle, rectangle, parallelogram, diamond, hexagon, and octagon. In such embodiment, when the inner cannula 14 is in its extended position, the first indicating member 48 and a part of the second indicating member 50 are perceptible through the viewing window 60. Particularly, the shaped puncture 76 of the first indicating member 48, for example a cross as shown in FIGS. 1 and 2, is exposed to or aligned with the viewing window 60 and the contrast color of the second indicating member 50 is perceptible through the shaped puncture 76. In addition, the shape itself may be perceptible regardless of the colors of the first indicating member and the second indicating member.

As shown in FIG. 2, the medical apparatus 10 further comprises means for introducing a fluid or gas into the insufflation needle 80. The gas is introduced into the handle 16 of the medical apparatus 10 via a gas inlet port 32 at the distal end 28 of the handle 16. The distal end 28 of the handle 16 is tapered and has a groove or waist which is arranged to receive and retain a conventional luer connector. The luer connector is coupled to a fluid extension or supply tube 30 at its distal end 28 and is further coupled to the gas inlet port 32 of the handle 16 at its opposite proximal end of the luer connector. Once the fluid or gas is introduced into the handle 16 via gas inlet port 32, the fluid or gas is further conducted by the resilient tube 18. The resilient tube 18 is disposed at a bottom surface of the bore 52 of the handle 16 and is configured to deliver the fluid or gas from the gas inlet port 32 to a gas outlet port 34. The gas outlet port 34 is located at the front end 68 of a switch body 66 of the handle 16 near the proximal end of the inner cannula 14.

The switch body 66 is generally a rectangular shape and is positioned in the switch section 84 of the handle 16. The switch body 66 includes the gas actuating switch 36 which controls the fluid or gas flow of the medical apparatus 10. The gas actuating switch 36 includes a sliding member 22 and a lever 20 and is configured to control the flow of the fluid or gas into the insufflation needle 80. The switch body 66 further includes horizontal grooved rails 72 on each side of the switch body 66 that are configured to slidably engage the sliding member 22 of the gas actuating switch 36. The sliding member 22 has a generally cylindrical superior surface that is configured to be engaged by the user. The sliding member 22 further includes horizontally extending arms 74, or fingers, that extends from both ends of the sliding member 22 and partially conforms to the exterior surface of the grooved rails 72 of the switch body 66. The extending arms 74 may be resiliently designed such that they may be biased (bent, formed, etc.) in a direction normal to the exterior surface of the grooved rails 72. At least a portion of the interior surfaces of the extending arms 74 contact the exterior surface of the grooved rails 72, thereby providing a sliding motion between the switch body 66 and the sliding member 22.

Figure 7:
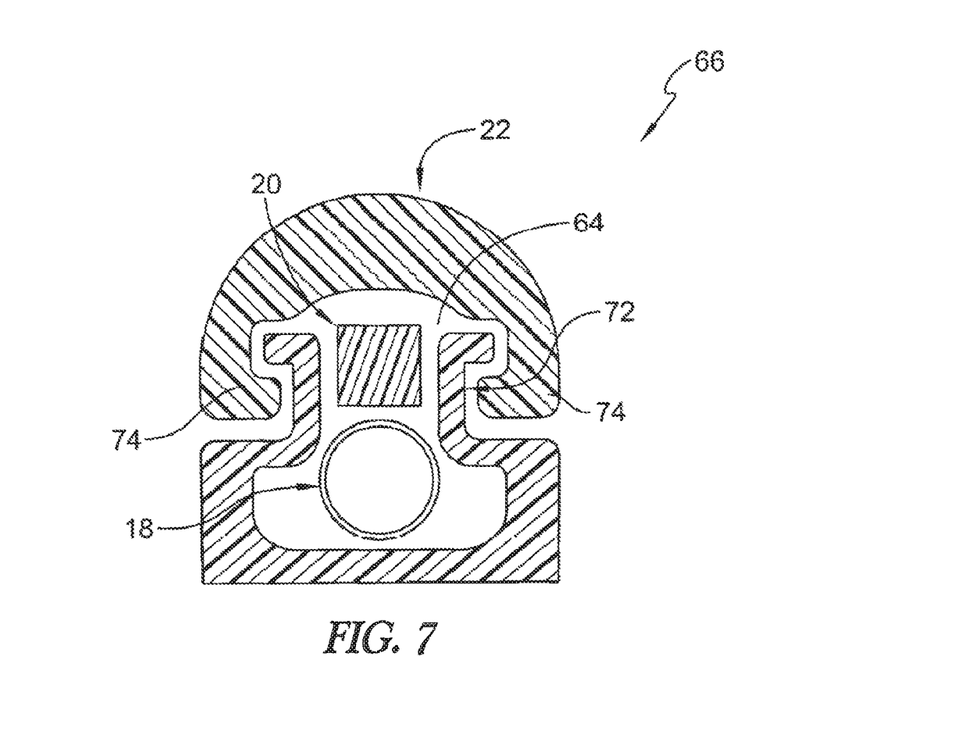
FIG. 7 is a cross section view taken along the line 7-7 in FIG. 6 showing the gas activation switch mechanism having a switch body, a lever, a sliding member, and a resilient tube.
Figure 8:
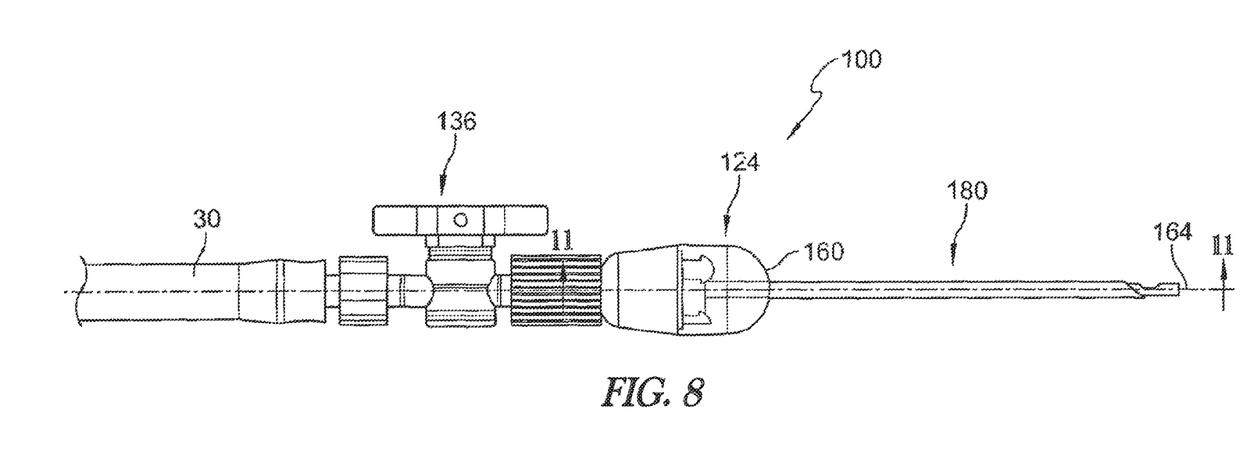
FIG. 8 is a side view of another embodiment of a surgical apparatus.

The switch body 66 further includes a horizontal slot 64. The slot 64 has a horizontally directed hole at the front end 68 of the switch body 66 and is spaced apart from the resilient tube 18 at the bottom of the switch body 66, as shown in FIG. 7. The slot 64 is configured to receive the lever 20 of the gas actuating switch 36. The lever 20 is an elongated rod and when assembled, the lever 20 is horizontally aligned on top of the resilient tube 18 and extends for a portion of the length of the switch section 84. The front end of the lever 20 is horizontally and slidably coupled to the slot 64. The other opposite distal end 78 of the lever 20 is arcuate inwardly toward the resilient tube 18. The arcuate distal end 78 of the lever 20 is positioned at a rear end 70 of the switch body 66 which creates an elevation at the rear end 70 compared to a front end 68 of the switch body 66. The exterior surface of the lever 20 is configured to be received by the interior surface of the sliding member 22 so that the sliding member 22 is slidable along the switch body 66 to allow the gas actuating switch 36 to slide between the first, "off," or compressed position and a second, "on," or released position. As described previously, the sliding member 22 is positioned at the superior surface of the handle 16 so that it can be controlled using the thumb or other digit of the user's hand that is holding the medical apparatus 10 which allows one-hand operation by the user to operate the medical apparatus 10.

The gas actuating switch 36 is in its compressed position when the sliding member 22 is moved backwardly toward the distal end 28 of the handle 16. Due to the arcuate distal end 78 of the lever 20 at the rear end 70 of the switch body 66, the sliding member 22 requires a force to be moved backwardly toward the user of the medical apparatus 10. When the sliding member 22 is moved back toward the rear end 70 of the switch body 66, the exterior surface of the lever 20 is received by the interior surface of the sliding member 22 and the arcuate distal end 78 of the lever 20 is pressed downwardly against the resilient tube 18, thereby pinching or crimping and occluding the resilient tube 18 to stop the gas flow. In addition, the resiliency of the resilient tube 18 creates a bias force against the exterior surface of lever 20 against the sliding member 22, thereby providing the appropriate amount of frictional resistance for the sliding action of the gas actuating switch 36.

In use, the insufflation needle 80 is inserted into the patient's body and the gas actuating switch 36 is in its released position to insufflate the surgical site. The gas actuating switch 36 is in its released position when the sliding member 22 is moved forwardly toward the front end 68 of the switch body 66. As the sliding member 22 slides forwardly along the switch body 66, the sliding member 22 disengages with the arcuate distal end 78 of the lever 20 and slides downwardly along the lever 20 toward the lower, front end 68 of the switch body 66, thereby releasing the pressure against the resilient tube 18. Therefore, when the gas actuating switch 36 is in its released position, the fluid or gas is allowed to flow through the handle 16 via the resilient tube 18 towards the insufflation needle 80. Specifically, the gas or fluid flows into the inner cannula 14 of the insufflation needle 80 via the gas outlet port 34 at the front end 68 of the switch body 66. The inner cannula 14 is hollow to allow the insufflation through the sufflation inlet aperture 40 to the sufflation outlet aperture 38 of the inner cannula 14. The sufflation inlet aperture 40 is formed near the proximal tip 62 of the inner cannula 14 and provides a means for allowing the fluid or gas to flow into the insufflation needle 80. Whereas, the sufflation outlet aperture 38 is formed near the distal blunt tip 44 of the inner cannula 14 and provides a means for allowing the fluid or gas to flow outward from the insufflation needle 80.

When the gas actuating switch 36 is back in its compressed position by moving the sliding member 22 backward toward the rear end 70 of the switch body 66, the fluid or gas flow stops and the internal abdominal pressure, for example, is sealed, so that pneumoperitoneum is maintained.

In some embodiments, the fluid or gas extension tube 30 may further include a ridge, flange, shoulder, or waist, which may facilitate connection with for example a threaded stop-cock or valve. Illustratively, the handle 16, or portions thereof such as for example the viewing window 86, may be fashioned out of clear or transparent poly-carbonate while the insufflation needle 80 may be made of suitable metal, for example stainless steel. For example, portions of the handle or manipulation portion may be opaque while the viewing window is clear. It will be appreciated, however, that the medical device 10 may be made from any metallic, non-metallic, or composite materials or any combinations thereof using any method of manufacture appropriate to the materials used including without limitation injection molding. For example, the tube(s) could be made in whole or in part from titanium, platinum, silver, gold, brass, bronze, aluminum, lead, copper, chrome, vanadium, martensite chrome steel, steel, stainless steel, plastic, kevlar, poly-carbonate, and the like or any combination thereof. Similarly, parts may be connected using any appropriate means known to those skilled in the art. The gas actuating switch 36 illustratively may be of the single pole, double throw type. In addition, the wiring and other components may be of any suitable construction, for example and without limitation, gold plating and/or copper or silver wiring may be used.

Referring now to FIGS. 8-11, another embodiment of a medical apparatus 100 is shown. The medical apparatus 100 comprises a stopcock valve 136, a position indication system 124, and an insufflation needle 180. A posterior end 140 of the stopcock valve 136 is configured to engage a supply tube 30 that is configured to supply fluid or gas to an insufflation needle 180. An anterior end 144 of the stopcock valve 136 is configured to engage the position indication system 124. The stopcock valve 136 has a generally cylindrical body 140 that allows fluid to flow from the posterior end 140 to the anterior end 144 of the stopcock valve 136. The stopcock valve 136 further includes a stopcock switch 138 which is configured to control the fluid flow.

Figure 9:
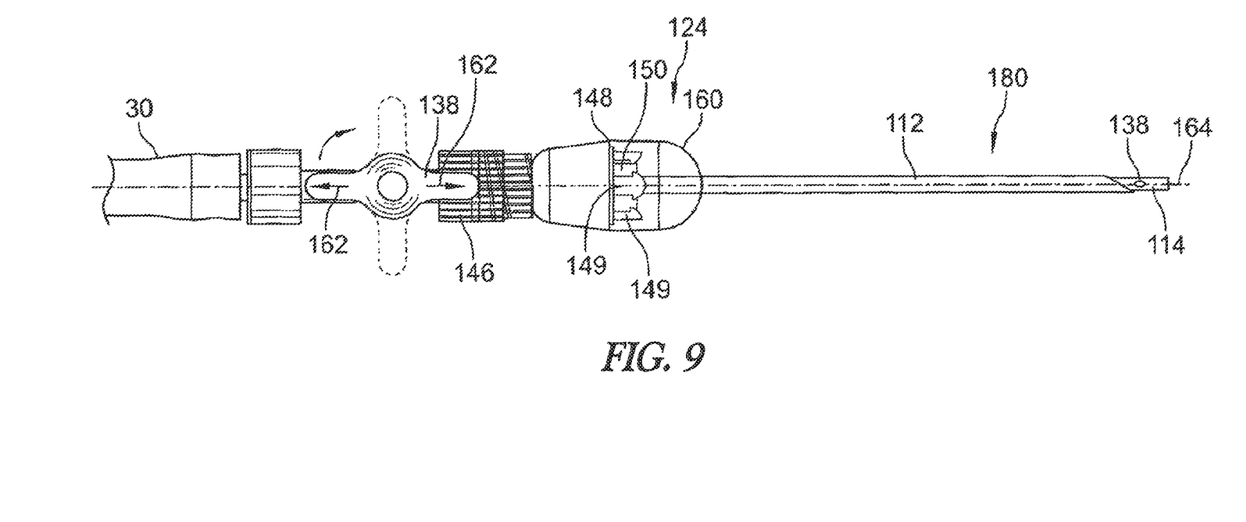
FIG. 9 is a top plan view of the surgical apparatus of FIG. 8.

Referring to FIG. 9, the stopcock valve 136 has two positions: an open position (illustrated in solid lines) and a closed position (illustrated in dotted lines). When the stopcock valve 136 is in the open position, the stopcock switch 138 is positioned such that arrows 162 of the switch 138 align with the longitudinal axis 164 of the medical apparatus 10. This allows fluid to flow from the supply tube 30 into the insufflation needle 180. To stop fluid from flowing into the insufflation needle 180, the stopcock switch 138 is rotated 90 degrees from the open position such that the arrows 162 of the switch 138 are perpendicular to the longitudinal axis 164.

Figure 10:
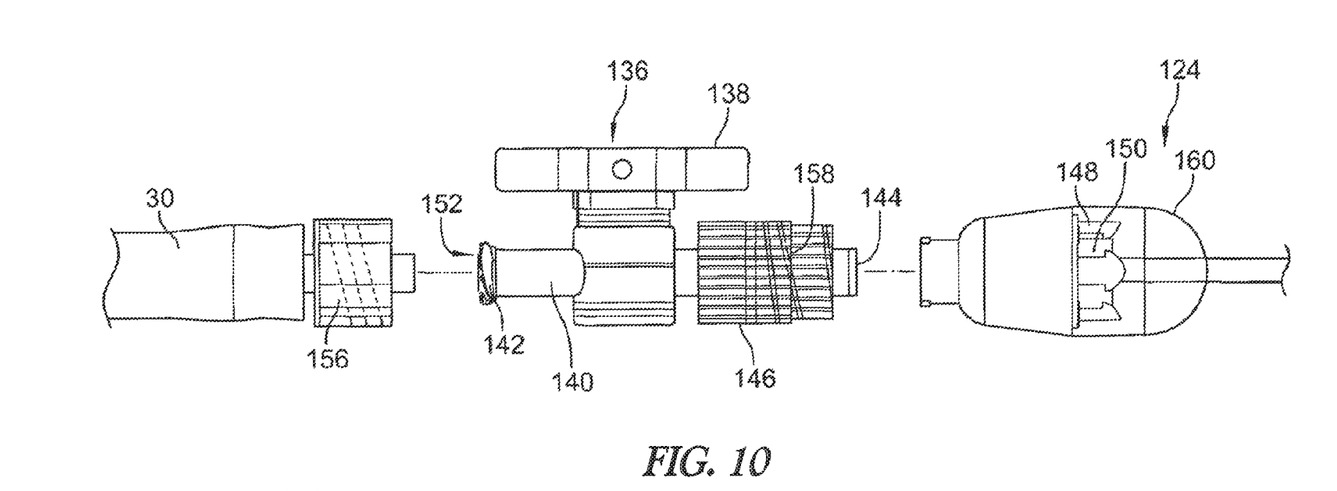
FIG. 10 is an exploded view of the surgical apparatus of FIG. 8.

In some embodiments, as shown in FIG. 10, the stopcock valve 136 is a 2-way stopcock, which includes Luer taper connections at both ends. The posterior end 142 of the stopcock valve 136 has a female Luer taper that is configured to receive a male Luer taper of the supply tube 30, which includes a plurality of threads 156. The female Luer taper of the stopcock valve 136 includes a tabbed hub 152 which screws into the plurality of threads 156 of the male Luer taper in order to secure the supply tube 30 to the stopcock valve 136. It should be appreciated that in some embodiments, an ergonomically designed handle may be positioned between the female Luer taper of the stopcock valve 136 and the male Luer taper of the supply tube 30.

In addition, an outer surface of the stopcock valve 136 at the anterior end 144 is tapered to provide a male Luer taper and includes a male Luer lock connector 146 having a plurality of inner threads 158. The male Luer taper of the stopcock valve 136 is adapted to fit into the female Luer taper of the position indication system 124. When the stopcock valve 136 and the position indication system 124 are held by friction, the connection may be further secured by rotating the male Luer lock connector 146 to screw the female Luer taper into the inner threads 158 of the connector 146. While the stopcock valve 136 is configured to engage the posterior end of the position indication system 124, the anterior end of the position indication system 124 is designed to be coupled to the insufflation needle 180.

Similar to the insufflation needle 80, the insufflation needle 180 is made up of a hollow outer cannula 112 and an inner cannula 114. As shown in FIG. 10, the outer cannula 112 and the inner cannula 114 are generally elongated. The inner cannula 114 has a smaller diameter than the hollow outer cannula 112 so that the inner cannula 114 is slidably received within and extends through the outer hollow cannula 112.

The outer cannula 112 and the inner cannula 114 each have a distal end and a proximal end. The proximal ends of both the outer cannula 112 and the inner cannula 114 are coupled to the position indication system 124. Specifically, the first end of the outer cannula 112 is affixed to the position indication system 124, and the first end of the inner cannula 112 is coupled to a moveable indicating member of the position indication system 124 as discussed in more detail below. The second end of the outer cannula 112 has a sharpened tip 142 that is relatively sharp to provide a means for puncturing body tissue, whereas the second end of the inner cannula 114 has a blunt tip 144 relative to the sharpened tip 142. The inner cannula 114 further includes two side sufflation holes or apertures, a sufflation outlet aperture 138 and a sufflation inlet aperture 140, to conduct the fluid or gas to the distal end of the insufflation needle 180, as will be described in more detail below.

The position indication system 124 includes a first indicating member 148 and a second indicating member 150 that are configured to indicate the position of the inner cannula 114. In the illustrative embodiment, the position indication system 124 includes an opaque portion at a distal half of the position indication system 124 and a generally dome-shaped clear viewing window 160 at the proximal half of the position indication system 124. The significantly large viewing window 160 protects the first and second indicating members 148, 150 and allows the first and second indicating members 148, 150 to be easily perceived, sensed or seen by a user. In the illustrative embodiment, the viewing window 160 is clear and extends 360 degrees circumferentially around the position indication system 124 so that the position indicating members 148, 150 are visible from any angle of view. In some embodiments, a clear portion of the viewing window 160 may extend less than 360 degrees, for example, 180 degrees circumferentially around the position indication system 124.

Figure 11:
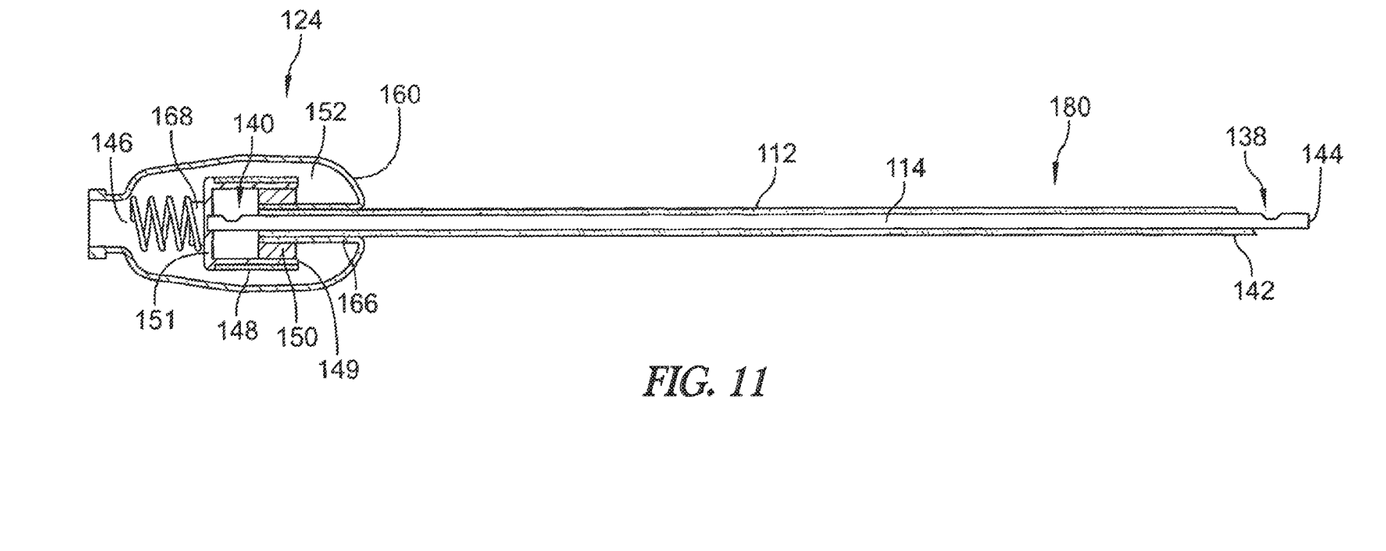
FIG. 11 is a cross sectional view taken along the line 11-11 in FIG. 8 showing a position indication system and an insufflation needle.

As shown in FIG. 11, the position indication system 124 further includes a hollow interior cavity 152 and inner walls 166 that extends inwardly from a proximal end of the position indication system 124. The inner walls 166 create a generally cylindrical shape which is configured to receive the insufflation needle 180. Specifically, the first end of the outer cannula 112 is affixed to the distal end of the inner walls 166. The first end of the inner cannula 114, on the other hand, extends through the inner walls 166 into the interior cavity 152 and is coupled to the first indicating member 148.

The second indicating member 150 of the position indication system 124 is affixed at the distal end of the inner wall 166 of the position indication system 124. Specifically, the second indicating member 150 has a generally cylindrical ring shape having an inner cylindrical surface. The inner surface of the second indicating member 150 is sized to receive the distal end of the inner wall 166 of the position indication system 124. Whereas, the first indicating member 148 is slidably coupled to the second indicating member 150. The first indicating member 148 includes a plurality of teeth 149. Each tooth 149 has an arrow shape with an arrowhead pointing to the proximal end of the insufflation needle 180. Illustratively, each tooth is evenly spaced apart from one another over the circumference of the second indicating member 150. The plurality of teeth 149 are connected at a distal plate 151 of the first indicating member 148 as shown in FIG. 11. The first indicating member 148 further includes a protrusion 168 extending distally from the distal plate 151, which is configured to engage a bias member 146. The bias member 146 is positioned at a distal end of the first indicating member 148 between a distal end of the interior cavity 152 and the distal end of the distal plate 151.

When the force is applied to the distal blunt tip 144 of the inner cannula 114, the first end of the inner cannula 114 is pushed against the first indicating member 148 and thus transferring the force to the bias member 146, for example a spring, that is attached to the first indicating member 148. The bias member 146 allows the inner cannula 114 to move between an extended position and a retracted position relative to the outer cannula 112. The extended position is a protective and safe position which allows the blunt tip 144 of the inner cannula 114 to extend past or beyond the sharpened tip 142 of the outer cannula 112. The retracted position is an exposed and unsafe position in which the bias member 146 is compressed and in which sharpened tip 142 of the outer cannula 112 is exposed in order to puncture body tissue.

The position indication system 124 illustratively includes a dual color array having the first indicating member and the second indicating member in different colors. As described above, the first indicating member 148 slides over the second indicating member 150. The first indicating member 148 is colored in a positive manner, such as for example and without limitation green. The second indicating member 150 is colored in a negative fashion, such as for example and without limitation red. Illustratively, the desired colors could be chosen from any desired color in the color spectrum as further described herein. Illustratively, the colors are different and contrast.

In this way, when the inner cannula 114 is in its protective extended position, it is fully extended past the sharpened tip 142 of the outer cannula 112. Both the first, illustratively green, or positive indicating member 148 and the second, illustratively red, or negative indicating member 150 are shown in the viewing window 160 so that it can be perceived, sensed or seen by the user. However, when the blunt tip 144 is retracted, for example by resistance or a force applied to the blunt tip 144 of inner cannula 114 by for example body tissue, it forces the second indicating member 150, illustratively green, to retract into the opaque portion of the position indication system 124, thereby showing only the second indicating member 150, illustratively red, in the viewing window 160 so that the user perceives, senses or sees the negative indicating member in the viewing window 160. In this fashion, the viewer knows that the sharpened tip 142 of the outer cannula 112 is exposed, and that there is a likelihood of harm to the patient if the inner cannula 114 does not return to its initial extended position.

In the illustrative embodiment, the position indication system 124 of the medical apparatus 100 is a visible indication system which comprises two position indicating members: a first indicating member 148 and a second indicating member 150. However, it will be appreciated that in some embodiment, the medical apparatus 100 may comprise a plurality of the position indication systems with different perceptible means. For example and without limitation, the position indication system may comprise the visible indication system, an audible or aural indication system, or a tactile indication system. The medical apparatus 100 may comprise, for example, a combination of a visible indication system and a tactile indication system, may comprise a combination of a visible indication system and an audible indication system, and may comprise a combination of a visible indication system, a tactile indication system, and an audible indication system. Further, the visual indication system may comprise a mechanical indication system, an electronic indication system, a chemical indication system, an infra-red indication system, a visible light indication system, a radio frequency indication system or any combination of the foregoing, for example and without limitation an electro-mechanical indication system. Of course, there may be more than one type of visual indication system, alone or in combination with one or more of the other types of indication systems.

In some embodiments, the plurality of teeth of the first indicating member may have different shape other than the arrow to distinguish between the first indicating member and the second indicating member so that position indicating members are easily perceived by the user. The shaped of the plurality of teeth of the first indicating member is helpful especially for color-blind users using the medical apparatus 100. Illustratively, the desired shapes of each tooth could be chosen from any shape. For example and without limitation any shape of circle, semicircle, oval, crescent, star, heart, hourglass, and any polygon, including but not limited to, triangle, rectangle, diamond, hexagon, and octagon.

Although certain illustrative embodiments have been described in detail above, variations and modifications exist within the scope and spirit of this disclosure as described and as defined in the following claims.

The invention claimed is:

1. A medical apparatus comprising:
a handle having an interior chamber defined between a distal end and an operative end of the handle,
a gas actuating comprising a stopcock switch, a switch having a sliding member and a lever in abutting relation to each other, the sliding member being positioned at a superior surface of the handle, or both,
an outer cannula having a first end and a second end, the first end coupled to an operative end of the handle, and the second end comprising a sharpened tip,
an inner cannula having a first end and a second end, the second end comprising a blunt tip, the inner cannula being slidably disposed within the outer cannula,
a position indication system having a first indicating member and a second indicating member disposed within the interior chamber of the handle, the first and second indicating members being visible through at least one viewing window, the first indicating member having at least one shaped puncture visible through the viewing window to indicate a position of the inner cannula, and
a bias member having a front end and a rear end, the bias member disposed within the interior chamber between the position indication system and the first end of the inner cannula,
wherein, when a force sufficient to overcome the normal force of the bias member is applied to the blunt tip of the inner cannula, the inner cannula moves to a retracted position where the blunt tip no longer extends beyond the sharpened tip of the outer cannula, and
wherein the first indicating member comprises a positive indicating member and the second indicating member comprises a negative indicating member, the positive indicating member is perceptible when the blunt tip exposed beyond the sharpened tip, and the negative indicating member is perceptible when the sharpened tip is exposed beyond the blunt tip and wherein the first indicating member includes a plurality of teeth arranged around a circumference of the second indicating member.

2. The medical apparatus of claim 1, wherein the viewing window extends 360 degrees around the position indication system about a longitudinal axis of the medical apparatus.

3. The medical apparatus of claim 1; wherein each viewing window is configured to align with each shaped puncture.

4. The medical apparatus of claim 1, wherein the first indicating member is slidably coupled to the second indicating member to indicate a position of the inner cannula relative to the outer cannula, the second indicating member is stationary and is affixed at the operative end of the handle.

5. The medical apparatus of claim 1, wherein the positive indicating member is a first color and the negative indicating member is a second color that is different than the first color.

6. The medical apparatus of claim 5, wherein the positive indicating member comprises the shaped puncture which extends through the positive indicating member thereby exposing a part of the second color of the negative indicating member positioned beneath the shaped puncture.

7. The medical apparatus of claim 1, wherein the gas actuating switch is configured to control gas flow of the medical apparatus by engaging a resilient tube operatively connecting the distal end and the operative end of the handle to conduct gas, the sliding member of the gas actuating switch is slidably movable between a first position and a second position along the handle.

8. The medical apparatus of claim 1, wherein the gas activation system is positioned on the superior surface of the handle to allow a one-hand operation.

9. The medical apparatus of claim 8, wherein the handle is ergonomically designed such that the distal end of the handle is tapered and angled toward the floor so that the medical device is held by the user's fingers pressing the medical device against a heel of the hand, leaving the thumb free for movement to control the gas actuating switch.

10. A medical apparatus comprising:
a stopcock switch configured to control gas flow of the medical apparatus,
an outer cannula having a first end and a second end, the first end coupled to an operative end of the handle, and the second end comprising a sharpened tip,
an inner cannula slidably coupled to the outer cannula, the inner cannula having a first end and a second end, the first end coupled to a bias member, the second end comprising a blunt tip that extends outwardly beyond the sharpened tip of the outer cannula, and
a position indication system having a first indicating member, a second indicating member, and the bias member, the first and second indicating members being visible through a clear viewing window to indicate a position of the inner cannula, the viewing window extending 360 degrees circumferentially around the position indication system,
wherein the position indication system is configured to be coupled to the outer and inner cannulas at a first end and the stopcock switch at a second end opposite the first end
wherein the first indicating member comprises a positive indicating member and the second indicating member comprises a negative indicating member, the positive indicating member is perceptible when the blunt tip exposed beyond the sharpened tip, and the negative indicating member is perceptible when the sharpened tip is exposed beyond the blunt tip and wherein the first indicating member includes a plurality of teeth arranged around a circumference of the second indicating member, and
wherein, when a force sufficient to overcome the normal force of the bias member is applied to the blunt tip at the second end of the inner cannula, the first end of the inner cannula forces the bias member to retract such that the blunt tip no longer extends beyond the sharpened tip of the outer cannula.

11. The medical apparatus of claim 10, wherein the first indicating member is slidably coupled to the second indicating member to indicate a position of the blunt tip of the inner cannula relative to the sharpened tip of the outer cannula, the second indicating member is stationary and is affixed to the position indication system.

12. The medical apparatus of claim 10, wherein the positive indicating member is a first color and the negative indicating member is a second color that is different than the first color.

13. The medical apparatus of claim 10, wherein each tooth has an arrow shape with an arrowhead pointing to the sharpened tip of the outer cannula.

14. The medical apparatus of claim 10 further comprising an ergonomically designed handle coupled to the stopcock switch opposite the position indication system.

15. The medical apparatus of claim 1, wherein the plurality of teeth are evenly spaced apart from one another over the circumference of the second indicating member.

16. The medical apparatus of claim 10, wherein the plurality of teeth are evenly spaced apart from one another over the circumference of the second indicating member.

17. The medical apparatus of claim 10, wherein each tooth is independently shaped as a circle, semicircle, oval, crescent, star, heart, hourglass, triangle, rectangle, diamond, hexagon, and octagon.

* * * * *

UNITED STATES PATENT AND TRADEMARK OFFICE
CERTIFICATE OF CORRECTION

Page 1 of 1

PATENT NO. : 10,463,814 B2
APPLICATION NO. : 15/260782
DATED : November 5, 2019
INVENTOR(S) : Clement et al.

It is certified that error appears in the above-identified patent and that said Letters Patent is hereby corrected as shown below:

In the Claims

In Column 15, Line 54, in Claim 3, delete "claim 1;" and insert --claim 1,-- therefor Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*